United States Patent
Khalil et al.

(10) Patent No.: US 11,925,713 B1
(45) Date of Patent: Mar. 12, 2024

(54) REINFORCED POROUS COLLAGEN SHEET

(71) Applicant: KING FAISAL UNIVERSITY, Al-Ahsa (SA)

(72) Inventors: Hany Ezzat Khalil, Al-Ahsa (SA); Hairul Islam Mohamed Ibrahim, Al-Ahsa (SA); Muthukumar Thangavelu, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/116,964

(22) Filed: Mar. 3, 2023

(51) Int. Cl.
*A61L 15/32* (2006.01)
*A61L 15/40* (2006.01)
*A61L 15/42* (2006.01)
*A61L 15/44* (2006.01)

(52) U.S. Cl.
CPC ............ *A61L 15/325* (2013.01); *A61L 15/40* (2013.01); *A61L 15/425* (2013.01); *A61L 15/44* (2013.01); *A61L 2300/30* (2013.01)

(58) Field of Classification Search
None
See application file for complete search history.

(56) References Cited

U.S. PATENT DOCUMENTS

| 4,412,947 A | 11/1983 | Cioca |
| 4,948,540 A | 8/1990 | Nigam |
| 2006/0182787 A1 | 8/2006 | Jaenichen et al. |
| 2018/0085408 A1* | 3/2018 | Moavenian ............ A61K 8/988 |
| 2022/0040378 A1 | 2/2022 | Thomas et al. |

FOREIGN PATENT DOCUMENTS

| EP | 1595527 A2 | 11/2005 |
| JP | 2014101355 A | 6/2014 |
| NZ | 188180 A | 12/1981 |
| WO | 0114202217 A1 | 8/2022 |

OTHER PUBLICATIONS

Doillon (Porous collagen sponge wound dressing: in vivo and in vitro studies), Technomic Publishing Co., Inc. (Year: 1988).*
Alfaqih et al. (The management of diabetic foot ulcer using the wound treatment techniques of modern dressing: A systematic review), Jurnal Ners, vol. 14, No. 3, Special issue (Year: 2019).*
Rocha et al. (Effect of honey and propolis, compared to acyclovir, against herpes simplex virus (HSV)-induced lesions: A systematic review and meta-analysis) Journal of Ethnopharmacology, 287 (Year: 2021).*
Vazhacharickal (A review on health benefits and biological action of honey, propolis and royal jelly), Journal of Medicinal Plants Studies, 9(5):1-13 (Year: 2021).*

(Continued)

*Primary Examiner* — Isis A Ghali
(74) *Attorney, Agent, or Firm* — Nath, Goldberg & Meyer; Richard C. Litman

(57) ABSTRACT

The reinforced porous collagen sheet includes a porous collagen sheet having Trigoneila *stellata* extract (TSE) and honey propolis (HP) incorporated therein. The porous collagen sheet can have various pore sizes and strong interconnectivity. The porous collagen sheets may have large pores, ranging in size from about 150 μm to about 500 μm.

5 Claims, 4 Drawing Sheets

(56) References Cited

OTHER PUBLICATIONS

Eldin et al. (A validated UPLC-PDA method for simultaneous determination of 3 biologically active isoflavans in Trigolla stellata extract), Natural Product Communications, vol. 15(7):1-6 (Year: 2020).*

Naga et al. (Methylisoflavan derivative from Trigolla stellata inhibited quorum sensing and virulence factors of Pseudomonas aeruginosa), World Journal of Microbiology and Biotechnology, 38:156 (Year: 2022).*

* cited by examiner

REINFORCED POROUS COLLAGEN SHEET

BACKGROUND

1. Field

The disclosure of the present patent application relates to wound healing, and more particularly to a reinforced porous collagen sheet including Trigoneila stellata extract (TSE) and honey propolis (HP).

2. Description of the Related Art

Wound healing is a complex process where the skin or another organ or tissue repairs itself after injury. In normal skin, the epidermis (outermost layer) and dermis (inner or deeper layer) form a protective barrier against the external environment. If the protective barrier is broken, the normal process of wound healing is immediately set in motion. Upon injury to the skin, a set of complex biochemical events takes place to repair the damage. The classic model of wound healing is divided into several sequential, yet overlapping phases. Effective wound healing requires the highly organized integration of complex molecular and biological events including cell proliferation, migration and extracellular matrix (ECM) deposition.

Healing may be promoted by restoring or preventing the breakdown of the skin or tissue/organ extracellular matrix. This may be accomplished through the addition of deficient components, such as collagen.

Collagen is a biodegradable protein and exists in a form of fibers in connective tissue of most animals. The primary function of collagen is to maintain the integrity of tissues and to provide tensile strength essential to tissues. At present, more than 21 different types of collagen have been discovered.

Collagen can be manufactured in different forms, such as sponge, gel, tube, or sheet. Manufactured collagen sheets can be applied as hemostats, wound dressings, drug carriers, scaffolds of artificial organs, fillers to recover tissues, or carriers for supporting cell growth. A porous collagen matrix can facilitate cell migration, cell growth or encapsulation and release of drugs. Processes for the preparation of a collagen matrix typically include comminuting starting materials generally by slicing or grinding, extraction, purification, lyophilization, and further comprising a cross-linking process. Acidic or alkaline collagens are generally used and cross-linked by a dehydrothermal process or by some chemical cross-linking agents, and lyophilized to obtain porous collagen matrices.

Further, although there are numerous wound healing products on the market, many consumers are hesitant to use chemically synthesized products perceived as being environmentally unfriendly or otherwise unsafe. Consequently, there is a need for wound healing products having natural components.

Thus, a reinforced porous collagen sheet solving the aforementioned problems is desired.

SUMMARY

A reinforced porous collagen sheet includes a porous collagen sheet including *Trigonella stellata* extract (TSE) and honey propolis (HP). The collagen sheet may be obtained from a bovine source. The porous collagen sheet can have various pore sizes and strong interconnectivity. The pores can range in size from about 150 μm to about 500 μm.

Wound healing can be accelerated by administering a therapeutically effective amount of the reinforced porous collagen sheet to a patient in need thereof. The reinforced porous collagen sheet may be topically administered.

These and other features of the present subject matter will become readily apparent upon further review of the following specification.

BRIEF DESCRIPTION OF THE DRAWINGS big. 1 is a chart of a cell viability assay of macrophages using the 3T3 cell line against different collagen scaffolds.

DETAILED DESCRIPTION OF THE PREFERRED EMBODIMENTS

Figure 1:
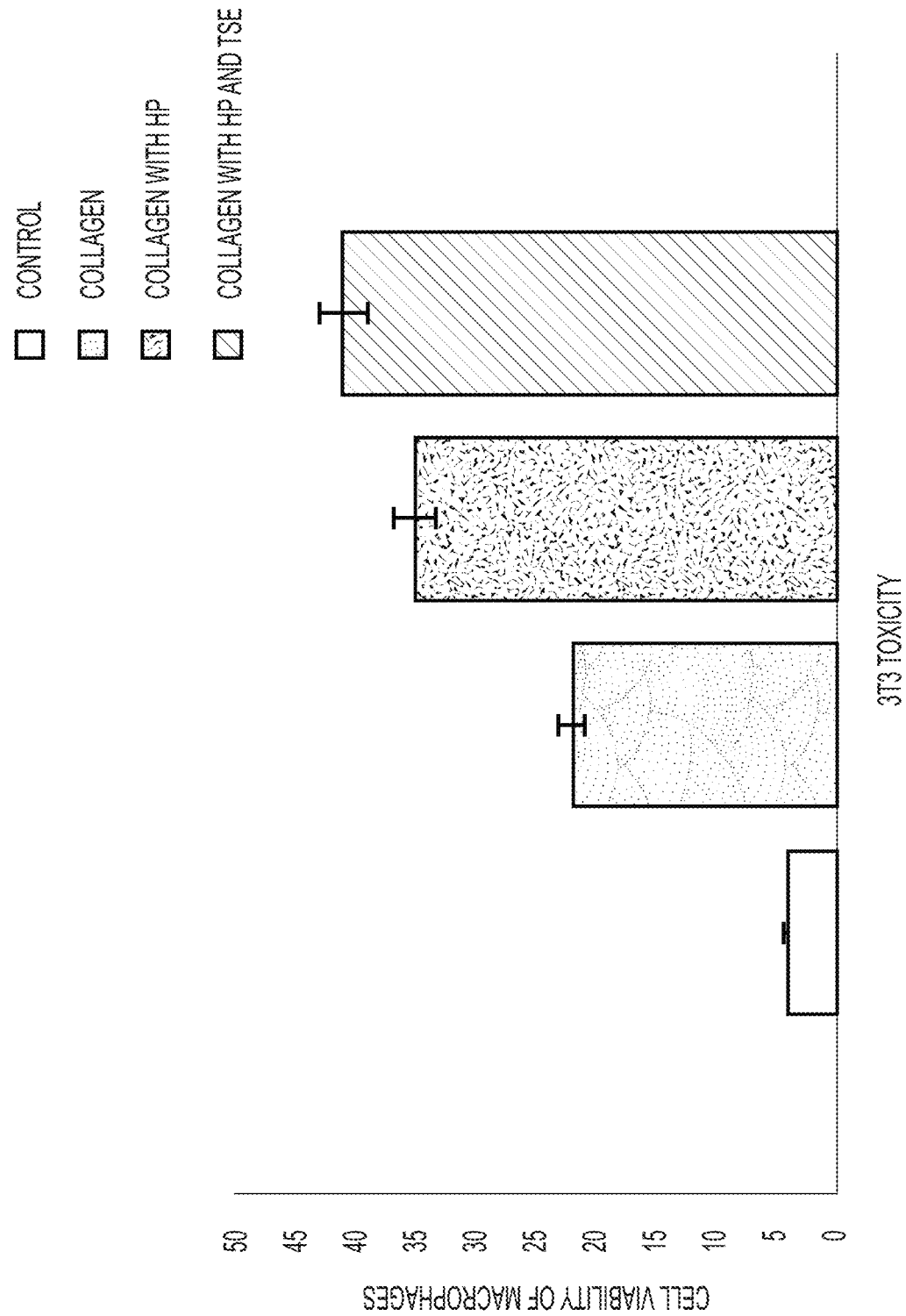

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the terra "about" refers to a ±10% variation from the nominal value unless otherwise indicated or inferred.

Unless defined otherwise, all technical and scientific terms used herein have the same meaning as commonly understood to one of ordinary skill in the art to which the presently described subject latter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Figure 2:
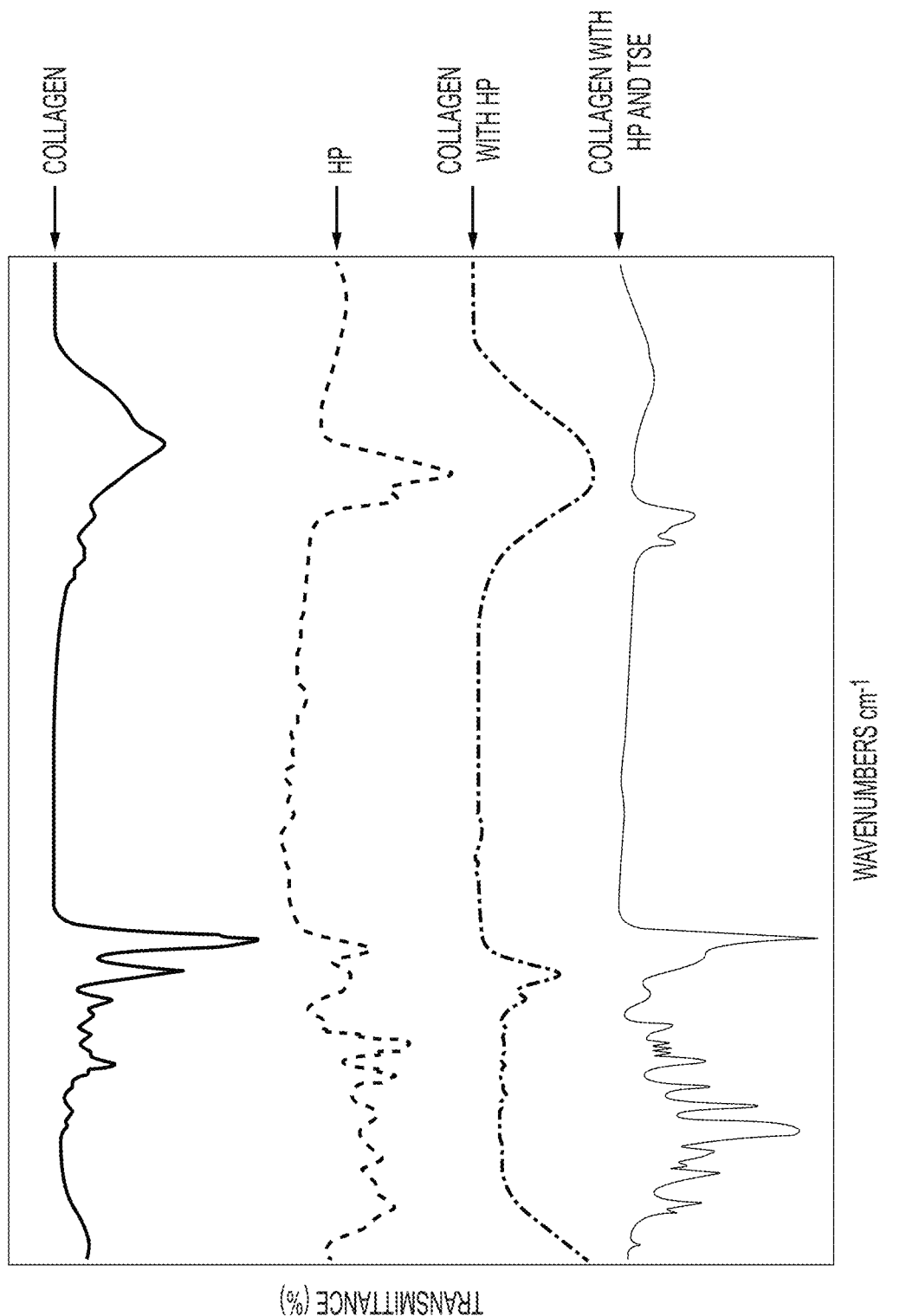
FIG. 2 is composite of Fourier transform infrared spectroscopy (FTIR) spectra comparing collagen sheet, honey propolis (HP), a collagen sheet with HP, and an exemplary reinforced porous collagen sheet.
Figures 3A, 3B, 3C, 3D, 3E, 3F, 3G, 3H:
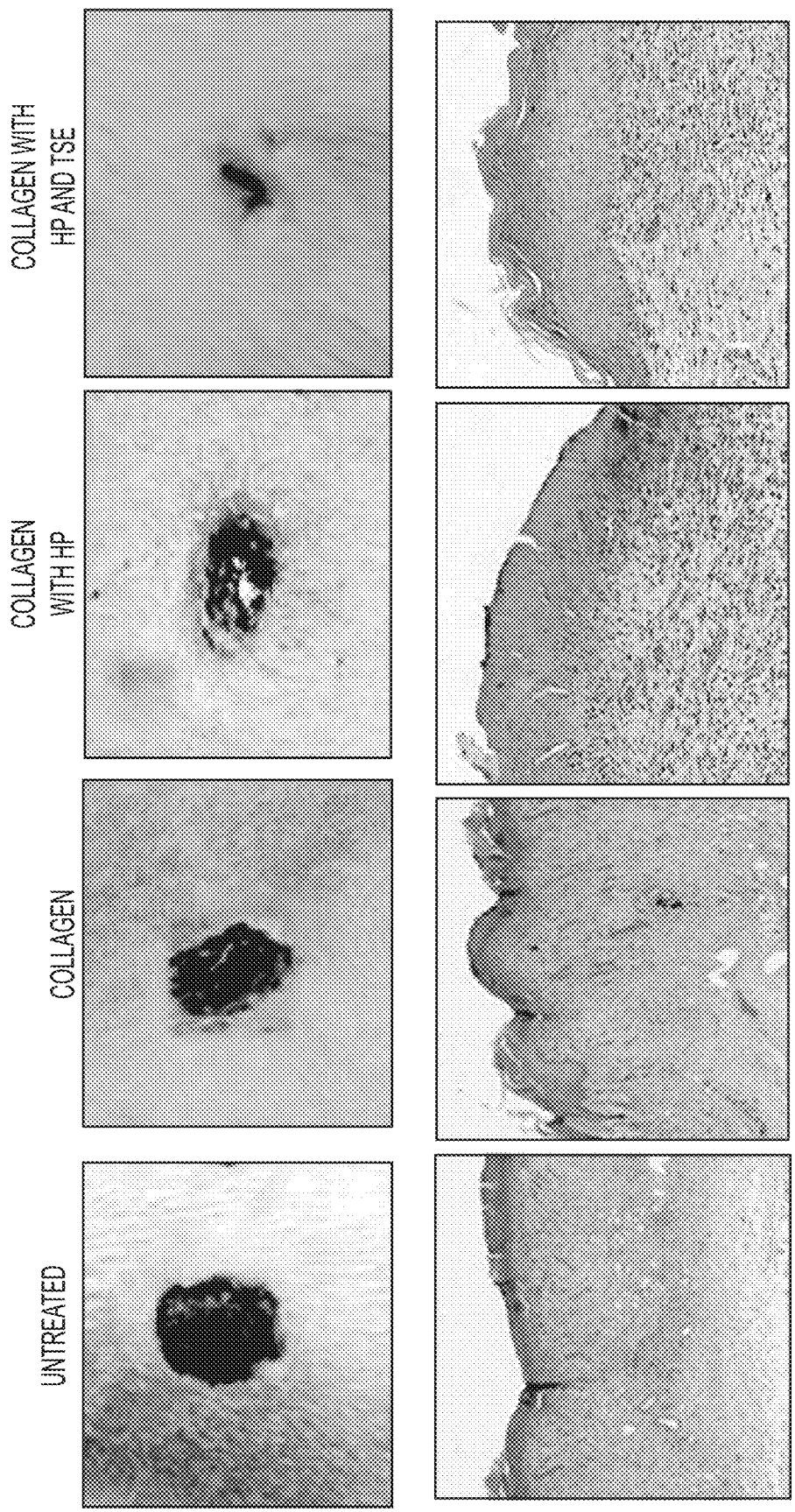
FIGS. 3A-3H is a table of micrographs showing histopathological and microscopic examination of wound healing under different treatment conditions.

The present disclosure is related to a reinforced porous collagen sheet including a porous collagen sheet loaded with Trigoneila stellata extract (TSE) and honey propolis (HP). Trigonella stellata extract (TSE) is known for having anti-inflammatory and antioxidant properties. Trigonella stellata constituents have been traditionally used to accelerate wound healing, to improve bone formation, and to heal skin diseases. Honey propolis (HP) is known for having antiseptic, anti-inflammatory, antioxidant, and antibacterial properties. The porous collagen sheet can have various pore sizes and strong interconnectivity. The pore sizes can range from about 150 μm to about 500 μm. For example, the pores may range in size from about 150 μm to about 250 μm. The reinforced porous collagen sheet may include from about 0.1% to about 2% collagen, from about 0.01% to about 1% of TSE, and from about 1 UM to 20 UM of HP In an exemplary embodiment, the reinforced porous collagen sheet can be prepared by extracting collagen from an animal source, combining the collagen with honey propolis (HP) and Trigonella stellata extract (TSE) to provide a first mixture; preparing an aqueous solution including the first mixture; mixing ice particulates with the aqueous solution to provide a second mixture; and freeze-drying the second mixture. Changes in functional groups and phase composition of the prepared collagen sheet were analyzed using fourier transform infrared spectroscopy (FTIR). FIG. 2 depicts the FTIR of a conventional collagen sheet, honey propolis, a collagen sheet including honey propolis (0.1 mg to 5 mg), and the exemplary reinforced porous collagen sheet (0.1 mg to 10 mg). The spectrum encompassed wavelengths ranging from 500 $cm^1$ to 4000 $cm^1$.

The collagen can be extracted from an animal source using ultrasonic extraction. In an embodiment, sonication, e.g., coupled ultra-sonication milling (CUM), can be used to combine the collagen, the honey propolis (HP) and the Trigonella stellata extract (TSE). The aqueous solution may include, for from about 0.1% to about 2% collagen, from about 0.01% to about 1% of TSE, and from about 1 UM to 20 UM of HP. The aqueous solution may be acidic.

The ice particulates can be prepared using methods known in the art, including, e.g., spraying Milli Q water into liquid nitrogen using a sprayer. The ice particulates can be sieved to obtain ice particulates having diameters of 150-250, 250-355, 355-425 and 425-500 μm.

Collagen can be obtained from connective tissue of any suitable animal, e.g., cow, pig, sheep, chicken, duck, turkey, goose, whale, or shark. The connective tissue can include skin, dermis, subcutaneous tissue, ligament, tendon, aponeurosis, cartilage, bone tissue, cornea, sclera, aorta, vessel, and the like. Preferably, the collagen is obtained from a bovine source, e.g., bovine tendon.

Wound healing can be accelerated by administering a therapeutically effective amount of the reinforced porous collagen sheet to a patient in need thereof. In particular, the reinforced porous collagen sheet can initiate cell proliferation and inhibit microbial activity. For example, the reinforced porous collagen sheet may be antimicrobial or exhibit anti-microbial activity. As set forth in Table I below, in an experiment, the reinforced porous collagen sheet demonstrated significant inhibition of microbial pathogens such as Salmonella typhi and Staphylococcus epidermis when compared to the inhibitory activity of collagen sheets prepared without HP and TSE, and collagen sheets including HP but without TSE. It is believed that timely release of the HP and TSE from the reinforced porous collagen sheet (FIG. 4) contributes significantly to the anti-microbial property of the reinforced collage sheet.

TABLE 1

Anti-microbial activity (Minimum inhibitory concentrations [mm])

| Texting mixture | Salmonella typhi | Staphylococcus epidermis |
|---|---|---|
| Collagen | — | — |
| Collagen with HP | 9.1 | 9.8 |
| Collagen with HP and TSE | 13.2 | 15.3 |

Wound healing can be accelerated by administering a therapeutically effective amount of the reinforced porous collagen sheet to a patient in need thereof. The reinforced porous collagen sheet may be topically administered. The reinforced porous collagen sheet can initiate cell proliferation at the wound site and inhibit microbial activity.

The present teachings are illustrated by the following examples.

Example 1

Collagen Sheet Preparation

Trigonella vellum (1 kg) was collected, washed thoroughly, dried, coarsely ground and then extracted with hydro-alcohol solvent (80% ethanol using distilled water (3×3000 mL)). Subsequently, the resulting liquid extracts were compiled and dried using rotary evaporator to obtain the dried extract, which was kept in the freezer at 4° C. for further use.

Collagen solution with a concentration of 1% (w/v) was prepared in 2.5% (v/aqueous acetic acid and biphasic sodium (concentration 2%). The porous scaffold sheets were prepared by a freeze-drying methodology. Collagen with and without HP (0.1 mg to 5 mg) and with and without TSE (0.1 mg to 10 mg) were mixed in various rheological and stoichiometry ratios with 0.25% glutaraldehyde (GA, 0.25 ml) solution and added as cross-linking active molecules with collagen agent. The solution was homogenized and degassed with 10 µV sonication for 15 min. The final mixture was transferred to a cryo-slab plastic container and kept in −80° C. overnight, then freeze dried for 24 hours and stored at 4° C.

Example 2

Cell Viability and Toxicity

The reinforced porous collagen sheet was tested immurine fibroblasts (3T3 cell lines). The viability of the cells 3T3 that adhered to the surface of the scaffolds collagen sheet with and without HP (0.1 mg to 5 mg) and with and without TSE (0.1 mg to 10 mg)) was assessed using a Live/Dead Viability kit (Dojindo) including tetrazolium salt. The reinforced porous collagen sheet initiated significantly more cellular proliferation than that exhibited by collagen sheets prepared without HP and TSE, and collagen sheets including HP but without TSE (see FIG. 1).

Histopathological and microscopic examination of wounds in mice under different treatment conditions demonstrated the effectiveness of the reinforced porous collagen sheet in wound healing. Male BalbC mice between 22 g and 26 g weights were divided into four groups containing five animals in each group (control, collagen, collagen with HP and collagen with HP and TSE). The mice were housed in groups during one week acclimation period prior to the study, housed individually later in 12 h light/dark cycle at 25±1° C. and were provided standard rodent feed with water ad libitum.

The dorsal surface of the mice below the cervical region was shaved after an intraperitoneal injection of standard anesthesia (ketamine −30 mg/kg body weight and xylazine −6 mg/kg body weight). A 1.5×2 cm full thickness excision wound was created. Control (group 1), wounds were dressed with sterile cotton gauze. Group 2 animals were dressed with the plain collagen sheet alone, group 3 animals with collagen with HP and group 4 animals with collagen with HP+TSF, bio composite sheet. The dressings were changed periodically at an interval of 3 days with respective dressing materials. Wound tissues were removed by sacrificing five mice each from all groups periodically on the $10^{th}$ and $20^{th}$ days of post wound creation and the granulation tissues formed were collected and stored at −80° C. until analysis. The progress of wound healing in rats were evaluated by periodical monitoring of wound contraction area, and biochemical studies.

FIGS. 3A-3H are photographic images showing healing patterns of the excisional wounds, taken from the same distance. The regenerated skin tissues from the wound site periodically collected along with healthy skin of 2 mm surrounding the wound on the $10^{th}$ and $20^{th}$ days of post wound creation following euthanasia (injection of an overdose of sodium barbitopental). The samples were fixed in 10% buffered formalin, dehydrated with graded ethanol series, and then embedded in paraffin blocks. The samples were sliced into 4-µm sections and stained with hematoxylin and eosin (H&E, Fisher Scientific) to examine regeneration of the epidermis and dermis. The sections were examined under an optical microscope 40× and photomicrographs were taken. The results demonstrated that reinforced porous collagen sheet further promoted the expression and production of type 0.11 collagen and increased formation tissues and mechanical properties of cartilage and skeletal muscles.

Figure 4:
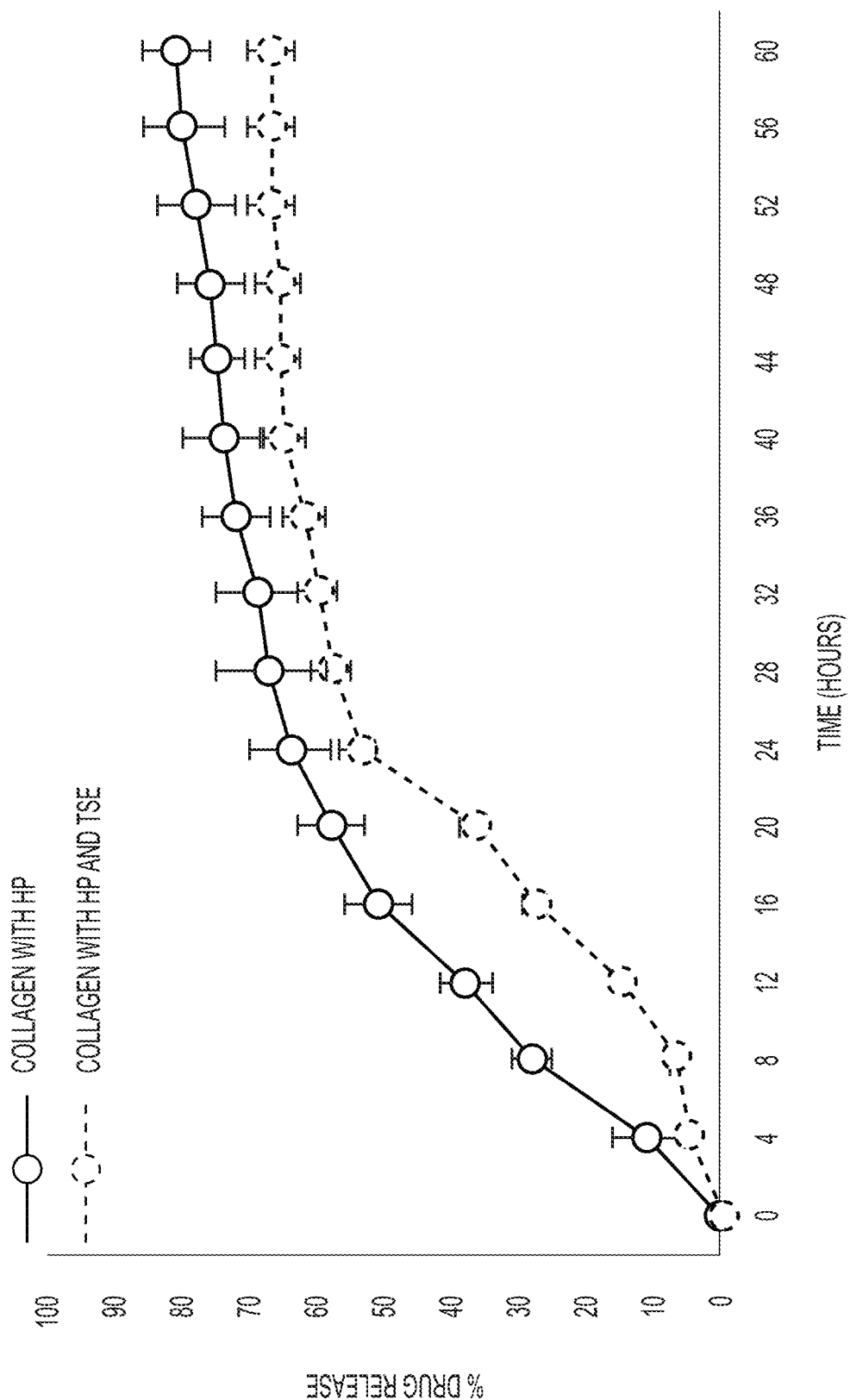
FIG. 4 is a graph comparing in vitro release of a collagen sheet with HP only to a collagen sheet including both HP and TSE components from an exemplary reinforced porous collagen sheet.

In vitro release of collagen with HP and collagen with HP+TSE was determined in triplicate at 37±0.1° C. using a modified dialysis apparatus (FIG. 4). A phosphate buffer (pH 7.4) was used as release medium. Aliquots of 2 mL were withdrawn from the release medium at different times and completed with the same volume of fresh buffer (of 37° C.). Concentration of HP and TSE were measured at 255 nm, and the cumulative amounts of bond broken between the collagen and LIP with TSE released were determined using the calibration curve.

It is to be understood that the reinforced porous collagen sheet is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of accelerating wound healing, comprising administering a therapeutically effective amount of a reinforced porous collagen sheet to a patient in need thereof, wherein the reinforced porous collagen sheet accelerates the wound healing by initiating cell proliferation and inhibiting microbial activity, and wherein the reinforced porous collagen sheet comprises from about 0.1% to about 2% collagen, from about 0.01% to about 1% *Trigonella stellata* extract (TSE) obtained using a hydro-alcohol solvent, and from about 1 UM to 20 UM honey propolis (HP), the porous collagen sheet having pores between about 150 µm to about 500 µm.

2. The method of claim 1, wherein the microbial activity is caused by at least one of *Salmonella typhi* and *Staphylococcus epidermis*.

3. The method of claim 1, wherein the pores range in size from about 150 µm to about 250 µm.

4. The method of claim 1, wherein the collagen is derived from a bovine source.

5. The method of claim 4, wherein the collagen is derived from bovine tendon.

\* \* \* \* \*